(12) United States Patent
Matsuura

(10) Patent No.: US 7,422,864 B2
(45) Date of Patent: Sep. 9, 2008

(54) METHOD FOR MEASURING OXIDIZED LDL-CRP COMPLEX AND MEASUREMENT KIT

(76) Inventor: Eiji Matsuura, 20-801, Nishinocho 7-chome, Okayama-shi, Okayama (JP)

( * ) Notice: Subject to any disclaimer, the term of this patent is extended or adjusted under 35 U.S.C. 154(b) by 0 days.

(21) Appl. No.: 10/546,321

(22) PCT Filed: Feb. 20, 2004

(86) PCT No.: PCT/JP2004/001961

§ 371 (c)(1),
(2), (4) Date: Dec. 15, 2005

(87) PCT Pub. No.: WO2004/074833

PCT Pub. Date: Sep. 2, 2004

(65) Prior Publication Data

US 2006/0194270 A1    Aug. 31, 2006

(30) Foreign Application Priority Data

Feb. 21, 2003  (JP)  ............... 2003-043571
Sep. 25, 2003  (JP)  ............... 2003-333927

(51) Int. Cl.
*G01N 33/00* (2006.01)

(52) U.S. Cl. .................. 435/7.94; 435/7.1; 435/7.92; 436/518; 436/164

(58) Field of Classification Search ............ 435/7.1, 435/7.92–7.95, 975; 436/501, 518, 524, 436/540, 164, 71
See application file for complete search history.

(56) References Cited

U.S. PATENT DOCUMENTS

| | | | |
|---|---|---|---|
| 4,933,275 A * | 6/1990 | Wands et al. ............. | 435/7.94 |
| 5,272,258 A * | 12/1993 | Siegel et al. ........... | 530/388.25 |
| 5,500,345 A * | 3/1996 | Soe et al. ............... | 435/7.1 |
| 5,900,359 A | 5/1999 | Matsuura et al. | |
| 6,432,632 B2 | 8/2002 | Nakayama et al. | |
| 2002/0150890 A1 | 10/2002 | Nakayama et al. | |
| 2002/0193949 A1* | 12/2002 | Fischer et al. ......... | 702/22 |
| 2003/0077668 A1 | 4/2003 | Uchida et al. | |
| 2005/0181451 A1* | 8/2005 | Bates ................... | 435/7.1 |

FOREIGN PATENT DOCUMENTS

EP    1 070 962 A2    1/2001
JP    2001-324506    11/2001
WO    95/09363    4/1995
WO    95-09363    4/1995

OTHER PUBLICATIONS

K. Kobayashi et al., "A specific ligand for $\beta_2$-glycoprotein I mediates autoantibody-dependent uptake of oxidized low density lipoprotein by macrophages", Journal of Lipid Research, vol. 42, pp. 697-709, 2001.

J. Hulthe et al., "Relationship between C-reactive protein and intima-media thickness in the carotid and femoral arteries and to antibodies against oxidized low-density lipoprotein in healthy men: the Atherosclerosis and Insulin resistance (AIR) study", Clinical Science, vol. 100, pp. 371-378, 2001.

M. Ryan et al., "Antibodies to oxidized lipoproteins and their relationship to myocardial infarction", QJ Med., vol. 91, pp. 411-415, 1998.

M. Chang et al., "C-reactive protein binds to both oxidized LDL and apoptotic cells through recognition of a common ligand: Phosphorylcholine of oxidized pohspholipids", PNAS, vol. 99, No. 20, pp. 13043-13048, Oct. 1, 2002.

C. Monaco et al., "Autoantibodies against oxidized low density lipoproteins in patients with stable angina, unstable angina or peripheral vascular disease", European Heart Journal, vol. 22, pp. 1572-1577, 2001.

Y. Hasunuma et al., "Involvement of $\beta^2$-glycoprotein I and anticardiolipin antibodies in oxidatively modified low-density lipoprotein uptake by macrophages", Clin. Exp. Immunol., vol. 107, pp. 569-573, 1997.

J. George et al., "Induction of Early Atherosclerosis in LDL-Receptor-Deficient Mice Immunized with $\beta_2$-Glycoprotein I", Circulation, vol. 98, pp. 1108-1115, 1998.

(Continued)

*Primary Examiner*—Long V. Le
*Assistant Examiner*—Gary W Counts
(74) *Attorney, Agent, or Firm*—Wenderoth, Lind & Ponack, L.L.P.

(57) ABSTRACT

The present invention provides a method for measuring a "complex of oxidized LDL and CRP" which comprises using an "anti-CRP antibody". An "anti-apoB antibody and/or anti-$\beta$2-GPI antibody" is preferably used in the method of the present invention, which preferably comprises at least a step for forming a sandwich complex represented by "the anti-apoB antibody and/or anti-$\beta$2-GPI antibody"-"the complex of oxidized LDL and CRP"-"the anti-CRP antibody". Either the "anti-apoB antibody and/or anti-$\beta$2-GPI antibody" or the "anti-CRP antibody" is preferably immobilized on a solid phase. According to the measuring method of the present invention, the "complex of oxidized LDL and CRP" may be simply, promptly and easily measured with high sensitivity, high accuracy at a lower cost.

3 Claims, 5 Drawing Sheets

OTHER PUBLICATIONS

P. Holvoet et al., "Oxidized LDL and Malondialdehyde-Modified LDL in Patients with Acute Coronary Syndromes and Stable Coronary Artery Disease", Circulation, vol. 98, pp. 1487-1494, 1998.

J. George et al., "Immunolocalization of $\beta_2$-Glycoprotein I (Apolipoprotein H) to Human Atherosclerotic Plaques", Circulation, vol. 99, pp. 2227-2230, 1998.

Q. Liu et al., "ω-Carboxyl variants of 7-ketocholesteryl esters are ligands for $\beta_2$-glycoprotein I and mediate antibody-dependent uptake of oxidized LDL by macrophages", Journal of Lipid Research, vol. 43, No. 9, pp. 1486-1495, 2002.

E. Matsuura et al., "Anti-$\beta_2$-Glycoprotein I Autoantibodies and Atherosclerosis", Intern. Rev. Immunol., vol. 21, pp. 51-56, Jan. and Feb. 2002.

J. George et al., Oxidized low-density lipoprotein (Ox-LDL) but not LDL aggravates the manifestations of experimental antiphospholipid syndrome (APS), Clin. Exp. Immunol., vol. 108, pp. 227-233, May 1997.

Chang et al., "C-Reactive protein binds to both oxidized LDL and apoptotic cells through recognition of a common ligand: Phosphorylcholine of oxidized phospholipids", Proc. Natl. Acad. Sci., vol. 99, pp. 13043-13048, 2002.

Mi-Kyung Chang et al., "*C-reactive protein binds to both oxidized LDL and apoptotic cells through recognition of a common ligand: Phosphorylcholine of oxidized phospholipids*", Proceedings of the National Academy of Sciences of USA, National Academy of Science, Washington, DC, vol. 99, No. 20, pp. 13043-13048 (2002).

Kazuko Kobayashi et al., "*Circulation oxidized LDL forms complexes with $\beta_2$-glycoprotein I: implication as an atherogenic autoantigen*", Journal of Lipid Research, vol. 44, pp. 716-726 (2003).

Eiji Matsuura et al., "*Oxidative modification of low-density lipoprotein and immune regulation of atherosclerosis*", Progress in Lipid Research, vol. 45, No. 6, pp. 466-486 (2006).

Masako Tabuchi et al., "*The association of C-reactive protein with an oxidative metabolite of LDL and its implication in atherosclerosis*", Journal of Lipid Research, vol. 48, pp. 768-781 (2007).

* cited by examiner

METHOD FOR MEASURING OXIDIZED LDL-CRP COMPLEX AND MEASUREMENT KIT

This application is a 371 U.S. National Stage application of International Application No. PCT/JP2004/001961, filed Feb. 20, 2004.

TECHNICAL FIELD

The present invention relates to a method for measuring a "complex of oxidized LDL and CRP" in the body fluid, and a kit used for measuring the same.

BACKGROUND ART

Abbreviations used in the specification will be described below.
APS: antiphospholipid syndrome
β2-GPI: β2-glycoprotein
β2-GPI-oxLDL complex: a complex of oxLDL and β2-GPI
β2-GPI-oxLDL-CRP complex: a triple complex among oxLDL, β2-GPI and CRP
BSA: bovine serum albumin
CRP: C-reactive protein
EDTA: ethylenediamine tetraacetic acid
ELISA: enzyme-linked immunosorbent assay
HRP: horseradish peroxidase
LDL: low density lipoprotein (non-oxidized native protein)
OD: optical density (absorbance)
oxLDL: oxidized LDL
oxLDL-CRP complex: a complex of oxLDL and CRP CRP is a serum protein that binds to phosphocholine of C-polysaccharide existing in the cell wall of Streptococcus pneumoniae, and is a kind of acute phase proteins (a group of proteins that increase in blood by inflammatory changes including infection).

CRP is described to bind to oxLDL in Proc. Natl. Acad. Sci., 99, p 13043-13048 (2002). However, neither measurement of the oxLDL-CRP complex present in the body fluid, nor clinical significance thereof is disclosed and suggested in the literature.

While International Patent Application Laid-Open (WO) No. 95/09363 describes the measurement of the "β2-GPI-oxLDL complex" in the body and clinical significance thereof, neither a disclosure nor a suggestion with regard to the "oxLDL-CRP complex" is found in the patent publication.

DISCLOSURE OF INVENTION

The present invention relates to a method for measuring an oxLDL-CRP complex present in a body fluid, a method for detecting diseases using the same, and a detection kit.

The inventor of the present invention has found, as a result of investigating the method for measuring the oxLDL-CRP complex, that the oxLDL-CRP complex can be simply, promptly and easily measured with high sensitivity, high accuracy at a lower cost by using an anti-CRP antibody. In addition, the inventor of the present invention has provided a kit used for the measurement, and thus accomplished the present invention.

The present invention provides a method for measuring the "oxLDL-CRP complex" in the body fluid, which comprises using an "anti-CRP antibody" (hereinafter, referred to as the "measuring method of the present invention"). Preferably, an "anti-apoB antibody and/or an anti-β2-GPI antibody" is also used in the measuring method of the present invention.

Preferably, the measuring method of the present invention comprises a step for forming a sandwich complex represented by an "anti-apoB antibody and/or an anti-β2-GPI antibody"-"oxLDL-CRP complex"-"anti-CRP antibody".

Preferably, either the "anti-apoB antibody and/or anti-β2-GPI antibody" or "anti-CRP antibody" is immobilized on a solid phase.

While specific steps for forming the sandwich complex are not particularly limited, the "anti-apoB antibody and/or anti-β2-GPI antibody" may be allowed to react with the "oxLDL-CRP complex" followed by allowing the "anti-CRP antibody" to react with the reaction product, the "oxLDL-CRP complex" may be allowed to react with "anti-CRP antibody" followed by allowing the "anti-apoB antibody and/or anti-β2-GPI antibody" to react with the reaction product, or these antibodies and the complex may be allowed to simultaneously react.

The measuring method of the present invention preferably contains the following steps 1 to 3:

(Step 1) a step for forming a first complex represented by an "antibody A immobilized on a solid phase"-"oxLDL-CRP complex" by allowing the solid phase on which antibody A is immobilized to contact a body fluid;

(Step 2) a step for forming a sandwich complex represented by an "antibody A immobilized on the solid phase"-"oxLDL-CRP complex"-"antibody B" by allowing the first complex formed in the step 1 to contact antibody B; and (Step 3) a step for detecting the sandwich complex formed in step 2.

"Antibody A" means any one of antibodies of the "anti-apoB antibody and/or anti-β2-GPI antibody" and "anti-CRP antibody", and "antibody B" means the other antibody.

The body fluid used in the measuring method of the present invention is preferably blood (serum or plasma).

The present invention also provides a method for detecting diseases comprising the steps of measuring the "oxLDL-CRP complex" in the body fluid by using the measuring method of the present invention, and correlating the measured "oxLDL-CRP complex" with the diseases (hereinafter, referred to as the "detection method of the present invention").

The disease detected by the detection method of the present invention is preferably selected from the group consisting of APS, thrombosis, arterial thrombosis, venous thrombosis, pregnancy morbidity, renal diseases and diabetes.

The present invention also provides a kit for measuring the "oxLDL-CRP complex" in the body fluid comprising the following constituting components (A) and (B) (hereinafter, referred to as the "kit of the present invention"):

(A) a solid phase on which antibody A is immobilized; and
(B) antibody B.

"Antibody A" means either "anti-apoB antibody and/or anti-β2-GPI antibody" or "anti-CRP antibody", and "antibody B" means the other antibody.

The kit of the present invention is preferably used for detecting diseases.

The measuring method of the present invention is quite useful since the oxLDL-CRP complex in the body fluid can be simply, promptly and easily measured with high sensitivity, high accuracy at a lower cost, and furthermore, the method provides the detection method and the kit of the present invention. Since the CRP-oxLDL complex and CRP-oxLDL-β2-GPI complex have been suggested to be risk factors of diseases such as arteriosclerosis and diabetes, the detection method of the present invention is quite useful since the method is able to detect various diseases including arteriosclerosis and diabetes by measuring the oxLDL-CRP complex. The kit of the present invention is also quite useful since the measuring method and detection method of the present invention may be simply, promptly and readily practiced using the kit of the present invention.

BEST MODE FOR CARRYING OUT THE INVENTION

Figure 1:
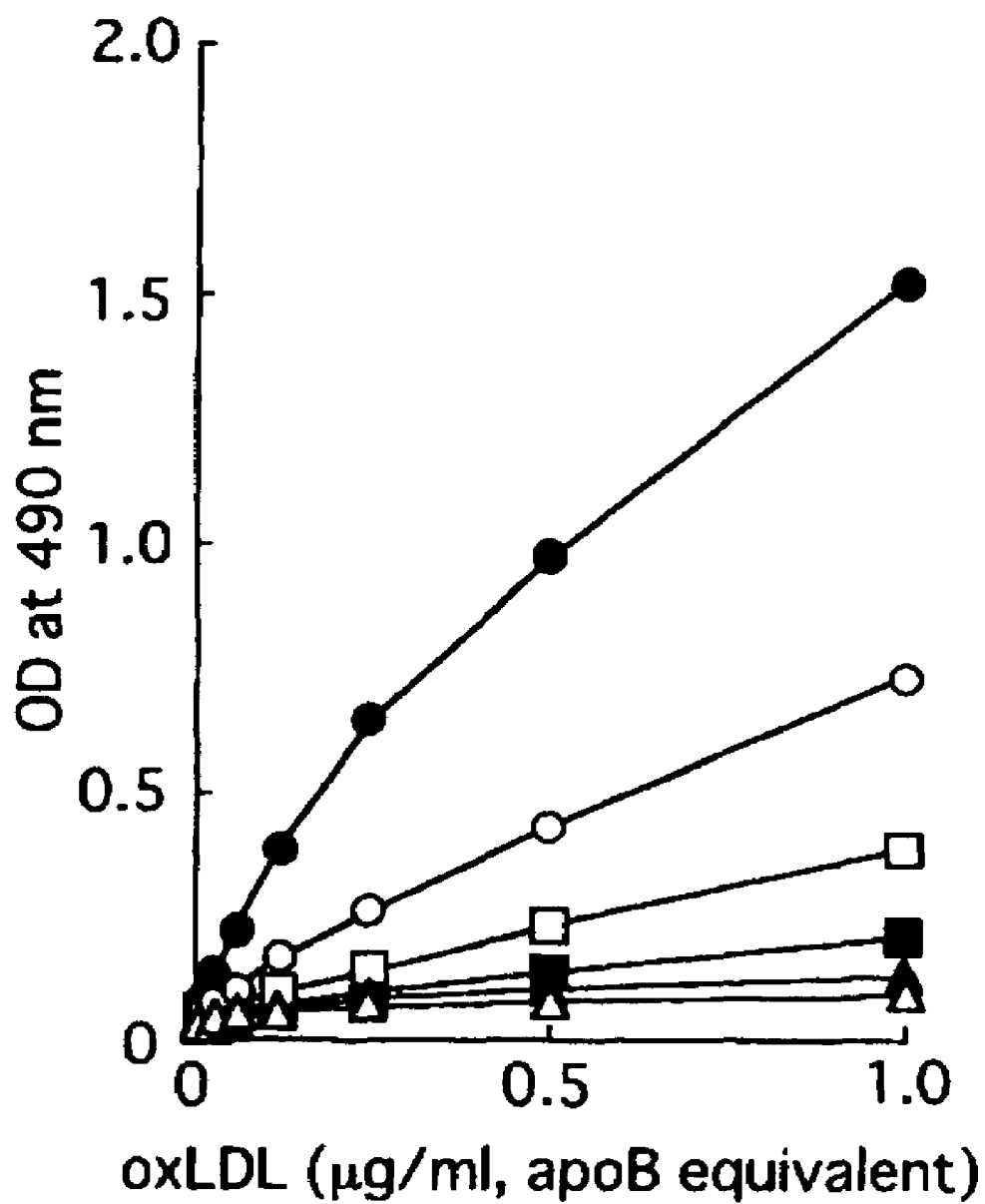
FIG. 1 shows the results of detection of the oxLDL-CRP complex by sandwich method using immobilized anti-apoB antibody and HRP-labeled anti-CRP antibody.

The embodiments of the present invention will be described below.

<1> Measuring Method of the Present Invention

The measuring method of the present invention is a method for measuring the "oxLDL-CRP complex" in the body fluid, which comprises using the "anti-CRP antibody".

The term "measurement" in this specification is a concept not only for quantitatively measuring a substance, but also for qualitatively detecting a substance (detecting the presence or absence of the substance).

While the "anti-CRP antibody" is not particularly limited so long as it is an antibody that binds to CRP, it is preferable that the antibody specifically binds to CRP. The antibody may be either a monoclonal antibody or a polyclonal antibody. Both the monoclonal anti-CRP antibody and polyclonal anti-CRP antibody can be prepared according to a conventional method for preparing the antibody using CRP as an antigen. Commercially available anti-CRP antibody may be directly used. A specific example of the antibody immobilized on a plate is anti-CRP antibody PG-021 (manufactured by Nippon Biotest Laboratories inc.), and a specific example of the labeled antibody for detection is anti-CRP antibody A80-125P (manufactured by Bethyl Laboratories Inc.).

While the measuring method of the present invention is not particularly limited so long as the "oxLDL-CRP complex" in the body fluid is measured by using the anti-CRP antibody, it is more preferable to use the "anti-apoB antibody and/or anti-β2-GPI antibody" further.

While the "anti-apoB antibody" used herein is not particularly limited so long as it is an antibody that binds to apoB, it is preferable that the antibody specifically binds to apoB. A monoclonal antibody and polyclonal antibody of this antibody may be also prepared according to a conventional method for preparing the antibody using apoB as an antigen. A commercially available anti-apoB antibody may be directly used. Specific examples of the anti-apoB antibody include N2E10 (established by Department of Cell Chemistry, Graduate School of Medicine, Dentistry and Pharmaceutical Sciences, Okayama University, available from the laboratory) and 1D2 (manufactured by YAMASA CORPORATION).

While the "anti-β2-GPI antibody" used herein is not particularly limited so long as it is an antibody that binds to β2-GPI, it is preferable that the antibody specifically binds to β2-GPI. The monoclonal antibody and polyclonal antibody of this antibody may be also prepared according to conventional methods for preparing antibody by using β2-GPI as an antigen. The commercially available anti-β2-GPI antibodies may be directly used. Specific examples of the antibody include WB-CAL-1 (described in J. Immunol., 149, p 1063-1068 (1992)), Cof-22 and Cof-23 (described in Blood, 87, p 3262-3270 (1996)) and EY2C9 (described in Arthritis Rheum., 37, p 1453-1461 (1994)).

β2-GPI is known to specifically binds to oxLDL but not to LDL (non-oxidized, native LDL). It is also known that oxLDL is bonded to β2-GPI in the body fluid. Accordingly, using the "anti-β2-GPI antibody" in the measuring method, detection method and kit of the present invention means to measure the "β2-GPI-oxLDL-CRP complex" in the body fluid.

"apoB" is a protein found in LDL. Accordingly, using the "anti-apoB antibody" in the measuring method, detection method and kit of the present invention means to measure the "oxLDL-CRP complex" in the body fluid.

Specific methods of the measuring method of the present invention are not limited so long as the anti-CRP antibody is used in the method. Specific examples of the method include an immunological assay using an antibody (ELISA method (sandwich method, competitive method and inhibitory method), immunoblotting method and coagulation method).

While a specific step for further using the "anti-apoB antibody and/or anti-β2-GPI antibody" is not particularly limited, it is preferable that the step comprises a step for forming a sandwich complex represented by the "anti-apoB antibody and/or anti-β2-GPI antibody"-"oxLDL-CRP complex"-"anti-CRP antibody". In other word, the sandwich method is preferably used in the measuring method of the present invention. When the "anti-β2-GPI antibody" is used, the step contains at least a step for forming the sandwich complex represented by the "anti-β2-GPI antibody"-"β2-GPI-oxLDL-CRP complex"-"anti-CRP antibody".

The measuring method of the present invention preferably uses either the "anti-apoB antibody and/or anti-β2-GPI antibody" or the "anti-CRP antibody" immobilized on a solid phase.

The solid phase for immobilizing these antibodies is not particularly limited so long as it is able to immobilize the antibody and is insoluble in water, body fluid or measuring reaction solution. Examples of the configuration of the solid phase include plates (for example wells of a microplate), tubes, beads, membranes and gels. Examples of the material of the solid phase include polystyrene, polypropylene, nylon and polyacrylamide.

A plate using polystyrene as the material is preferable among them.

Generally used immobilizing methods for proteins and lipids such as a physical adsorption method and covalent bond method may be used as the method for immobilizing the antibody on the solid phase.

The physical adsorption method is preferable among them since the operation thereof is simple and the method is frequently used.

In the specific example of the physical adsorption method, the antibody is dissolved in a buffer solution, and the solution is made to contact the solid phase (for example microplate) to allow the antibody to be adsorbed on the solid phase.

When a portion of the surface on which the antibody is not immobilized remains on the surface of the solid phase, the "oxLDL-CRP complex" or other molecules may be immobilized there to impair accurate measuring results from being obtained. Accordingly, it is preferable to block the portions on which no antibody is immobilized by adding a blocking substance before permitting the body fluid to contact the solid phase. Examples of the blocking substance include serum albumin, casein, skim milk and gelatin. Commercially available blocking substances may be also used.

An example of the blocking method comprises adding the blocking substance (such as serum albumin, casein, skim milk and gelatin), followed by storing the solid phase at 37° C. for 30 minutes to 2 hours or at room temperature (15 to 25° C.) for 1 to 2 hours.

When a solid phase on which either the "anti-apoB antibody and/or anti-β2-GPI antibody" or "anti-CRP antibody" is immobilized is used, the method preferably comprises the following steps 1 to 3:

(Step 1) a step for forming a first complex represented by the "antibody A immobilized on the solid phase"-"oxLDL-CRP complex" by allowing the solid phase on which antibody A is immobilized to contact the body fluid;

(Step 2) a step for forming a sandwich complex represented by the "antibody A immobilized on the solid phase"-"oxLDL-CRP complex"-"antibody B" by allowing the first complex formed in step 1 to contact antibody B; and (Step 3) a step for detecting the sandwich complex formed in step 2.

"Antibody A" means either the "anti-apoB antibody and/or anti-β2-GPI antibody" or "anti-CRP antibody", and "antibody B" means the other antibody. When a solid phase on which the "anti-apoB antibody", "anti-β2-GPI antibody" or "both the anti-apoB antibody and anti-β2-GPI antibody" are immobilized is used in step 1, the "anti-CRP antibody" is made to contact in step 2. On the contrary, when a solid phase on which the "anti-CRP antibody" is immobilized is used in step 1, the "anti-apoB antibody", "anti-β2-GPI antibody" or "both anti-apoB antibody and anti-β2-GPI antibody" are made to contact in step 3.

When the "anti-β2-GPI antibody" is used, a sandwich complex represented by the "antibody A immobilized on the solid phase"-"β2-GPI-oxLDL-CRP complex"-"antibody B" is formed.

The "contact" method is not particularly limited so long as the molecule of the "antibody A immobilized on the solid phase" and the molecule of the "oxLDL-CRP complex", and the molecule of the "oxLDL-CRP complex" and the molecule of the "antibody B" contact with each other.

For permitting the intermolecular bond to be as perfect as possible after the "contact", the reaction system is preferably incubated. While the incubation time is not particularly limited so long as the antigen-antibody reaction between the "oxLDL-CRP complex" and antibody A or antibody B is not inhibited, the temperature is, for example, about 0 to 37° C. The incubation time is also not particularly limited, and may be appropriately selected by those skilled in the art. Usually, a longer incubation time permits the bond to be more perfectly formed.

It is also preferable to insert a washing operation between steps 1 and 2 and steps 2 and 3, respectively.

"Detection of the sandwich complex formed in step 2" is not particularly limited so long as a sandwich complex comprising the "antibody A immobilized on the solid phase"-"oxLDL-CRP complex"-"antibody B" is detectable, the "antibody B" present at an open end of the sandwich complex ("antibody B" not immobilized on the solid phase) is preferably detected.

For this purpose, "antibody B" itself that is made to contact in step 2 is preferably labeled with a labeling substance for facilitating the detection.

When the "anti-β2-GPI antibody" is used, the sandwich complex represented by the "antibody A immobilized on the solid phase"-"β2-GPI-oxLDL-CRP complex"-"antibody B" is detected.

When the unlabeled "antibody B" is used, a "substance to be bonded to antibody B" labeled with a labeling substance may be used. An example of the "substance to be bonded to antibody B" is an antibody that specifically binds to immunoglobulin depending on animal or classes from which "antibody B (immunoglobulin)" is derived. For example, when "antibody B" is mice IgG1, anti-mouse IgG1 antibody may be used as the "substance to be bonded to antibody B".

"Antibody B" present in the sandwich complex comprising the "antibody A immobilized on the sold phase"-"oxLDL-CRP complex" (the "β2-GPI-oxLDL-CRP complex" when the "anti-β2-GPI antibody" is used)-"antibody B" formed in step 2 may be detected by detecting the labeling substance. This means that the sandwich complex is detected.

While examples of the labeling substance used for such labels include enzymes (peroxidase, alkaline phosphatase, β-galactosidase, luciferase, acetylcholine esterase and the like), fluorescent dye (fluorescein isothiocyanate (FITC) and the like), chemoluminescence substances (luminol and the like), biotin and avidin (including streptoavidin), the substance is not limited thereto so long as it is able to label usual proteins. The labeling method may be appropriately selected from known methods suitable for labeling, for example a glutaraldehyde method, periodic acid cross-linking method, maleimide cross-linking method, carbodiimide method and activated ester method (see "Tanpakushitu no Kagaku (Chemistry of Proteins", part II, TOKYO KAGAKU DOZIN CO., LTD, 1987). For example, the methods appropriately selected include a method for using a hydrazide derivative of biotin (Avidin-Biotin Chemistry: A handbook, 57-63, PIERCE CHEMICAL COMPANY., 1994) when biotin is used as the labeling substance, or a method described in Examined Japanese Patent Publication No. 63-17843 when fluorescein isothiocyanate is used.

The method for detection of the labeling substance may be appropriately selected by those skilled in the art depending on the labeling substance used. For example, when peroxidase is used as the labeling substance, the labeling substance may be detected by measuring the intensity of luminescence of the product by an enzymatic reaction as a change of absorbance after adding a luminescent substrate such as tetramethyl benzidine and o-phenylenediamine and hydrogen peroxide. When a fluorescent substance or chemoluminescent substance is used, the fluorescence or luminescence after the reaction is measured.

While the body fluid used in the measuring method of the present invention is not particularly limited, the blood is preferable. The term "blood" used in this specification is a concept including the serum and plasma. The blood may be directly used, or it may be used after dilution. The blood may be processed so long as it does not affect the oxLDL-CRP complex in the sample.

<2> Detection Method of the Present Invention

The detection method of the present invention is a method for detecting a disease comprising the steps of measuring the "oxLDL-CRP complex" in the body fluid by using the measuring method of the present invention, and correlating the measured "oxLDL-CRP complex" with the disease.

The level of the "oxLDL-CRP complex" in the sample is measured at first by the measuring method of the present invention. The measuring method of the present invention has been described above.

The "body fluid" used herein is not particularly limited so long as it is derived from an animal as an object for detecting the disease. Other descriptions with respect to the "body fluid" are the same as described in "<1> measuring method of the present invention". In the detection method of the present invention, the "β2-GPI-oxLDL-CRP complex" is detected when the "anti-β2-GPI antibody" is used.

Then, a disease is detected by correlating the "oxLDL-CRP complex" (the "β2-GPI-oxLDL-CRP complex" when the "anti-β2-GPI antibody is used") in the body fluid measured by using the measuring method of the present invention with the disease.

The term "measurement" as used in this specification is a concept not only a quantitative measurement but also a qualitative detection (detection of presence or absence), as has been described previously. Accordingly, the "measured oxLDL-CRP complex" as used herein may be the "quantity" (a result of a quantitative measurement) or the "presence or absence" (a result of a qualitative measurement) of the complex in the body fluid. The "quantity" may be a value (measured value) determined from a calibration curve or a correlation equation prepared by using a standard sample having a known concentration, or a relative value to a normal animal (an animal not suffering with the disease).

The quantity of the "oxLDL-CRP complex" may increase depending on a certain kind of diseases. When the quantity of the complex in the body fluid is higher than that in normal persons, the patient may be correlated to "be suffering from the disease" or "to have a high possibility suffering form the disease". When the quantity of the complex in the body fluid is equal to that of the normal persons, the patient may be correlated as "not being suffering from the disease" or "to have a low possibility of suffering from the disease".

The detection method of the present invention includes not only the detection of the presence or absence of diseases, but also includes the severeness of the disease. For example, when the amount of the complex is found to be increasing by periodically measuring the amount of the complex in the body fluid of an individual, the result may be correlated as "the disease is progressing" or "the disease is highly liable to progress". On the contrary, when the amount of the measured complex tends to decrease, the result may be correlated as "the disease is improving" or "the disease is highly liable to be improved". When no changes are found in the amount of the complex, the result may be correlated as "the disease condition (or normality) is not changed" or "the disease condition (or normality) is highly liable to be not changed".

The disease detected by the detection method of the present invention is preferably selected from the group consisting of APS, thrombosis, arterial thrombosis, venous thrombosis, pregnancy morbidity, renal diseases, arteriosclerosis (cerebral infarction, myocardial infarction and the like) and diabetes.

<3> Kit of the Present Invention

The kit of the present invention is a kit for measuring the "oxLDL-CRP complex" in the body fluid comprising the following constituting components (A) and (B):

(A) a solid phase on which antibody A is immobilized; and
(B) antibody B.

"Antibody A" means either the "anti-apoB antibody and/or anti-β2-GPI antibody" or the "anti-CRP antibody, and "antibody B" means the other antibody. When a solid phase on which the "anti-apoB antibody", "anti-β2-GPI antibody" or "both the anti-apoB antibody and anti-β2-GPI antibody" are immobilized is used as constituting component (A), the "anti-CRP antibody" may be used as the constituting component (B). On the contrary, when a solid phase on which the "anti-CRP antibody" is immobilized is used as constituting component (A), the "anti-apoB antibody", "anti-β2-GPI antibody" or "both the anti-apoB antibody and anti-β2-GPI antibody" may be used as constituting component (B). When the "anti-β2-GPI antibody" is used in the kit of the present invention, the "12-GPI-oxLDL-CRP complex" can be measured.

"Antibody B" is preferably labeled with a labeling substance. Descriptions of the labeling substance applicable are the same as that described in "<1> measuring method of the present invention".

While the kit of the present invention is not particularly limited so long as it contains constituting components (A) and (B), it may contain other constituting components.

Examples of other components that may be added to the kit of the present invention include a detection reagent of the labeling substance, an "antibody that recognizes antibody B" and a reagent that labels the "antibody that recognizes antibody B". The kit may contain a blocking substance, a washing solution, a sample diluent and an enzyme reaction stopper solution.

These constituting components can be stored and kept in respective separate vessels as a kit, which can be used according to the measuring method of the present invention.

The oxLDL-CRP complex may be measured using the kit of the present invention according to the measuring method of the present invention.

The kit of the present invention is preferably used for detecting diseases. The "disease" detected by the kit of the present invention is preferably selected from the group consisting of APS, thrombosis, arterial thrombosis, venous thrombosis, pregnancy morbidity, renal diseases, arteriosclerosis (cerebral infarction, myocardial infarction and the like) and diabetes. The diseases can be detected by using the kit of the present invention according to the detection method of the present invention.

The "body fluid" as used herein is not particularly limited so long as it is derived from animals as the object for detecting the diseases. Other descriptions on the "body fluid" are the same as those described in "<1> measuring method of the present invention".

Hereinafter, the present invention will be described in more detail by reference to examples and reference examples, but the present invention is not limited thereto.

1. Materials, Methods and Abbreviations Used in the Examples and Reference Examples The composition of "HBS" (Hepes buffered saline solution) was 10 mM of Hepes and 150 mM of NaCl (pH 7.4).

The composition of "solution A" was HBS containing 2 mM of $CaCl_2$ and 1 mM of $MgCl_2$.

The composition of "T-HBS" was HBS containing 0.05% of Tween 20.

"WB-CAL-1" (IgG2a, κ) is an anti-β2-GPI autoantibody. The antibody is derived from antiphospholipid syndrome model mouse (NZW×BXSB mouse), which does not react with free β2-GPI but is reactive to it after forming a complex with oxidized LDL (J. Immunol., 149, p 1063-068 (1992)).

"N2E10" (IgG2a, κ) is an anti-human apoB antibody, which is a monoclonal antibody derived from mice. Hybridoma was established at Department of Cell Chemistry, Graduate School of Medicine, Dentistry and Pharmaceutical Sciences, Okayama University, and is available from the laboratory. While this antibody is also called as "2E10", it is named as "N2E10" in this specification with a letter "N" at the head since it is obtained by immunizing a mouse using untreated (native) LDL derived from human as an antigen.

"anti-CRP antibody (catalogue No. PG-021; IgG)" is a anti-human CRP antibody derived from goat. It was manufactured by Nippon Biotest Laboratories inc.

"HRP labeled anti-CRP antibody" is an anti-human CRP antibody derived from goat and labeled with horseradish peroxidase. The antibody was manufactured by Bethyl Laboratories, Inc.

"CRP" used was manufactured by Chemicon International Inc.

"Immulon 2HB" is a 96 well micro-titer plate manufactured by Dynex, and was used as an ELISA plate.

"PBS" is phosphate buffered saline.

"T-PBS" is PBS containing 0.05% of Tween 20.

"S-PBS" is PBS containing 0.5% of skim milk and 10 mM of $MgCl_2$.

2. Measurement of Complex of oxLDL and CRP (a Method Using Anti-apoB Antibody)

(1) Sample Preparation

The following samples were prepared using two kinds of solvents, HBS or solution A (two kinds of solutions are prepared with different solvents per one sample). HBS and solution A used as the solvents were sterilized with a 0.22 μm filter.

a solution containing 100 μg/ml (final concentration, the same hereinafter) of CRP;

a solution containing 100 μg/ml each of β2-GPI and CRP;

a solution containing 100 μg/ml of LDL (native LDL; specific gravity 1.019<d<1.063) prepared from the plasma of a normal human subject by ultracentrifugation;

a solution containing 100 μg/ml each of LDL and CRP;

a solution containing 100 μg/ml of oxLDL obtained by oxidizing LDL at 37° C. for 12 hours in the presence of 5 μM of $CuSO_4$;

a solution containing 100 μg/ml each of oxLDL and CRP;

a oxLDL-β2-GPI complex obtained by incubating a solution containing 100 μg/ml each of β2-GPI and oxLDL at 37° C. for 16 hours;

a solution containing 50 μg/ml of the oxLDL-β2-GPI complex and 100 μg/ml of CRP; and a solution containing 100 μg/ml each of β2-GPI, oxLDL and CRP.

Samples were prepared by incubating them at 37° C. for 20 hours with hermetic sealing.

(2) Elisa

The following procedures were used for ELISA.

(a) Anti-human apoB antibody N2E10 (8 μg/ml, diluted with HBS) was added to an ELISA plate (Immulon 2HB) in a proportion of 50 μl/well. The plate was allowed to stand at 4° C. overnight with hermetic sealing to immobilize N2E10 on each well of the plate.

(b) Then, the plate was washed by adding 200 μl/well of HBS (or T-HBS) containing 0.05% of Tween 20, and this operation was repeated three times.

(c) HBS containing 2% of BSA was added in a proportion of 200 μl/well, and the plate was allowed to stand at room temperature for 1 hour.

(d) Among the samples prepared in (1) above, the samples incubated in solution A were diluted with solution A so that the final concentration of CRP or LDL is 1 μg/ml. The samples incubated in HBS not containing $Ca^{2+}$ were also diluted using HBS. Samples sequentially diluted twice starting from a concentration of 1 μg/ml were also prepared. Each diluted sample was added to the ELISA plate on which N2E10 was immobilized in a proportion of 100 μl/well. The samples were allowed to stand at 27° C. for 2 hours thereafter.

(e) The well containing the sample diluted with solution A, and the well containing the sample diluted with HBS were washed with 0.05% Tween 20 and T-HBS, respectively, three times.

(f) The HRP labeled anti-CRP antibody (1 mg/ml) was diluted with solution A or HBS 10.000-fold, and the diluted solution was added to the well in a proportion of 100 μl/well. The plate was allowed to stand at room temperature for 1 hour.

(g) The well was washed three times by the same method as in (e) above.

(h) o-phenylenediamine (4 mg) was dissolved in 10 ml of 0.1 M citrate buffer (pH 5.0). Hydrogen peroxide (30%, 10 μl) was added to the solution, and this mixed solution was added to each well in a proportion of 100 μl/well to develop a color.

(i) The reaction was stopped by adding 1 M sulfuric acid, and absorbance at 490 nm was measured.

The samples of CRP or LDL diluted to a final concentration of 1 μg/ml were detected with immobilized anti-apoB antibody and HRP-labeled anti-CRP antibody (detection of oxLDL-CRP complex). The results are shown in Table 1.

TABLE 1

| Ligand | Absorbance at 490 nm | |
|---|---|---|
| | In the presence of Calcium ion | In the absence of Calcium ion |
| CRP (1.0 μg/ml, equal quantity of apoB) | 0.068 ± 0.002 | 0.078 ± 0.003 |
| β2-GPI, CRP | 0.064 ± 0.005 | 0.079 ± 0.008 |
| Native LDL | 0.035 ± 0.007 | 0.057 ± 0.010 |
| Native LDL, CRP | 0.170 ± 0.003 | 0.158 ± 0.003 |
| oxLDL | 0.048 ± 0.002 | 0.068 ± 0.004 |
| oxLDL, CRP | 1.926 ± 0.059 | 1.131 ± 0.012 |
| oxLDL-β2-GPI | 0.041 ± 0.004 | 0.054 ± 0.006 |
| oxLDL-β2-GPI, CRP | 1.879 ± 0.025 | 0.817 ± 0.017 |
| oxLDL, β2-GPI, CRP | 1.694 ± 0.022 | 1.052 ± 0.033 |

The results of detection of the samples sequentially diluted twice starting from a concentration of 1 μg/ml are shown in FIG. 1. In FIG. 1, the black solid marks and white hollow marks represent the results measured in the presence and absence of $Ca^{2+}$ (2 mM), respectively. In FIG. 1, the triangles represent the results in the solution containing oxLDL and CRP, the circles represent the results in the solution containing the oxLDL-β2-GPI complex and CRP, and squares represent the results in the solution containing β2-GPI, oxLDL and CRP.

The results showed that the CRP-oxLDL complex or CRP-oxLDL-β2-GPI complex was formed by incubation at 37° C. for 20 hours depending on the presence of $Ca^{2+}$. This measuring system would be able to detect these complexes in the body, if any.

3. Measurement of Complex of oxLDL and CRP (Method a Using the Anti-β2-GPI Antibody)

The samples were prepared by the same method as in 2.(1) above. The ELISA method was the same as in 2.(2) above, except that step (a) in 2.(2) was changed as follows.

WB-CAL-1 (8 μg/ml; an antibody against β2-GPI, diluted with HBS) was added to the ELISA plate (Immulon 2HB) in a proportion of 50 1/well, and WB-CAL-1 was immobilized on the plate by allowing to stand at 4° C. overnight with hermetic sealing.

The samples of CRP or LDL diluted to a final concentration of 1 μg/ml were detected with the immobilized anti-β2-GPI antibody and HRP-labeled anti-CRP antibody. The results of detection of the "β2-GPI-oxLDL-CRP complex" are shown in Table 2.

TABLE 2

| Ligand | Absorbance at 490 nm | |
|---|---|---|
| | In the presence of Calcium ion | In the absence of Calcium ion |
| CRP (1.0 μg/ml, equal quantity of apoB) | 0.042 ± 0.003 | 0.058 ± 0.002 |
| β2-GPI, CRP | 0.031 ± 0.008 | 0.055 ± 0.001 |
| Native LDL | 0.036 ± 0.005 | 0.043 ± 0.005 |
| Native LDL, CRP | 0.061 ± 0.004 | 0.069 ± 0.003 |
| oxLDL | 0.042 ± 0.002 | 0.056 ± 0.001 |
| oxLDL, CRP | 0.133 ± 0.028 | 0.093 ± 0.005 |
| oxLDL-β2-GPI | 0.034 ± 0.002 | 0.045 ± 0.003 |
| oxLDL-β2-GPI, CRP | 1.523 ± 0.065 | 0.727 ± 0.009 |
| oxLDL, β2-GPI, CRP | 0.208 ± 0.014 | 0.381 ± 0.003 |

Figure 2:
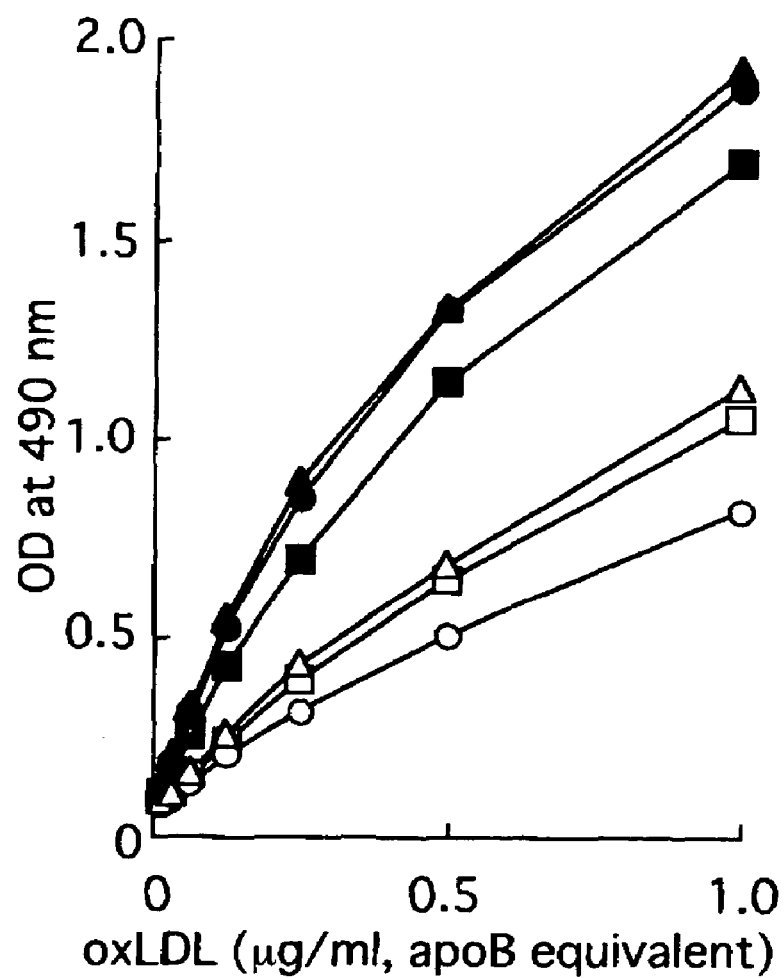
FIG. 2 shows the results of detection of the oxLDL-CRP complex by sandwich method using immobilized anti-β2-GPI antibody and HRP-labeled anti-CRP antibody.

The results of measurements of the samples sequentially diluted twice starting from a concentration of 1 μg/ml are shown in FIG. 2. The meanings of the marks in FIG. 2 are the same as those in FIG. 1.

The results showed that the CRP-oxLDL-β2-GPI complex was formed by incubation at 37° C. for 20 hours depending on the presence of $Ca^{2+}$. This measuring system would be able to detect these complexes in the body, if any.

4. Measurement of oxLDL-β2-GPI Complex (Reference Example: Method Using Immobilized Anti-β2-GPI Antibody and Anti-apoB Antibody)

The mouse monoclonal anti-β2-GPI antibody (WB-CAL-1; 8 μg/ml in PBS, pH 7.4) was added in each well of ELISA plate (Immulon 2HB) in a proportion of 50 μl/well. The plate was allowed to stand at 4° C. overnight to immobilize WB-CAL-1 on the plate.

Each well was washed three times by adding 0.05% Tween 20-containing PBS (T-PBS) in a proportion of 200 μl/well. Then, PBS containing 1% of skim milk was added to each well in a proportion of 200 μl/well, and the plate was allowed to stand at room temperature for 1 hour.

After discarding the blocking solution, a test sample appropriately diluted with PBS containing 0.5% of skim milk and 10 mM of $MgCl_2$ (S-PBS) was added to the plate on which WB-CAL-1 was immobilized in a proportion of 50 μl/well. The plate was allowed to stand at 27° C. for 2 hours, and each well was washed tree times with T-PBS.

Subsequently, biotinylated mouse monoclonal anti-apoB antibody (N2E10) was diluted with S-PBS to 0.2 μg/ml, the diluted sample was added in each well in a proportion of 100 μl/well, and the plate was allowed to stand at room temperature for 1 hour. After washing each well with T-PBS three times, horseradish peroxidase (HRP)-labeled streptoavidin (vector #SA-504. 1 mg/ml), which was diluted with S-PBS 1,500-fold, was added in each well in a proportion of 100 μl/well, and the plate was allowed to stand at room temperature for 30 minutes. After washing, a solution, prepared by dissolving 4 mg of o-phenylenediamine in 10 ml of 0.1 M citrate buffer (pH 5.0) and mixed with 10 μl of 30% hydrogen peroxide, was added in each well in a proportion of 100 μl/well to develop a color, and absorbance at 490 nm was measured.

5. Measurement of CRP-oxLDL Complex and CRP-oxLDL-β2-GPI Complex in Sera of Patient and Normal Person (1) Measurement High sensitivity CRP (hsCRP) in the sera (undiluted solution) of diabetic patients (138 cases) and normal persons (28 cases) was measured (control 1: FIG. 3(A)) as the quantity of CRP (mg/dl) by a highly sensitive CRP measurement method using "N-latex CRP (manufactured by Dade Behring Inc.). On the other hand, the oxLDL-β2-GPI complex (control 2: FIG. 3(B)), the CRP-oxLDL complex (example: FIG. 3(C)) and the CRP-oxLDL-β2-GPI complex (example: FIG. 3(D)) in the serum, each diluted 100-fold, were measured by methods "4.", "2." and "3." above, respectively.

In FIGS. 3(B), (C) and (D), the measured values are represented by units (U) calculated based on absorbance.

(2) Correlation Between the Results of Measurements

Correlation between the values measured in (1) was determined. The results of diabetic patients are shown in FIGS. 4(A), (B), (C) and (D), while the results of normal persons are shown in FIGS. 5(A), (B), (C) and (D).

(3) Discussion

Figure 3:
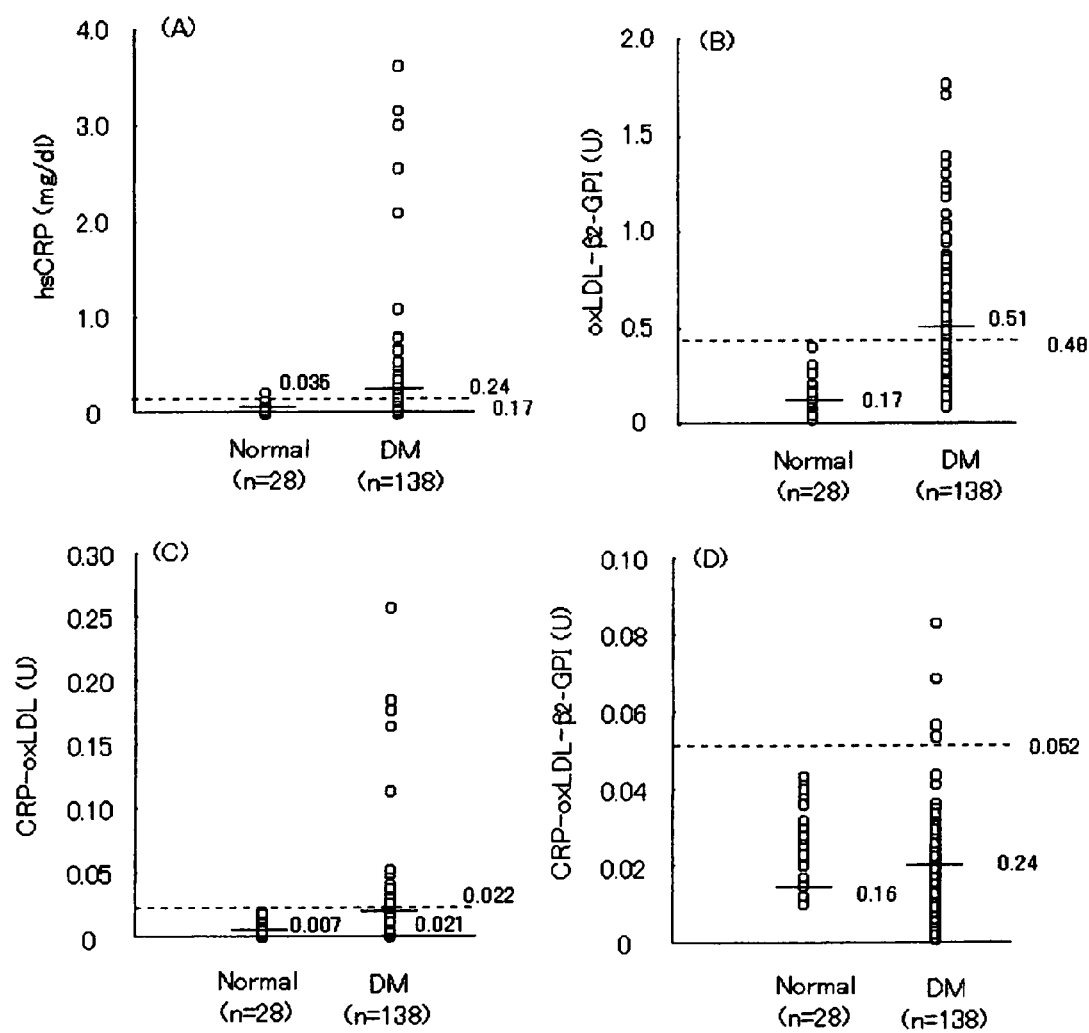
FIG. 3 shows the results of measurements of sera of diabetic patients (DM) and sera of normal persons (Normal). Graph (A) shows the results of the amount of CRP by highly sensitive CRP measurement, graph (B) shows the results of measurements of the oxLDL-β2-GPI complex by the method described in "4." in the example to be described hereinafter, graph (C) shows the results of measurements of the CRP-oxLDL complex by the method described in "2." in the example to be described hereinafter, and graph (D) shows the results of measurements of the CRP-oxLDL-β2-GPI complex by the method described in "3." in the example to be described hereinafter. The dotted horizontal line in each graph shows a cut-off value (average measured value of normal persons+3SD) in each measuring system.
Figure 4:
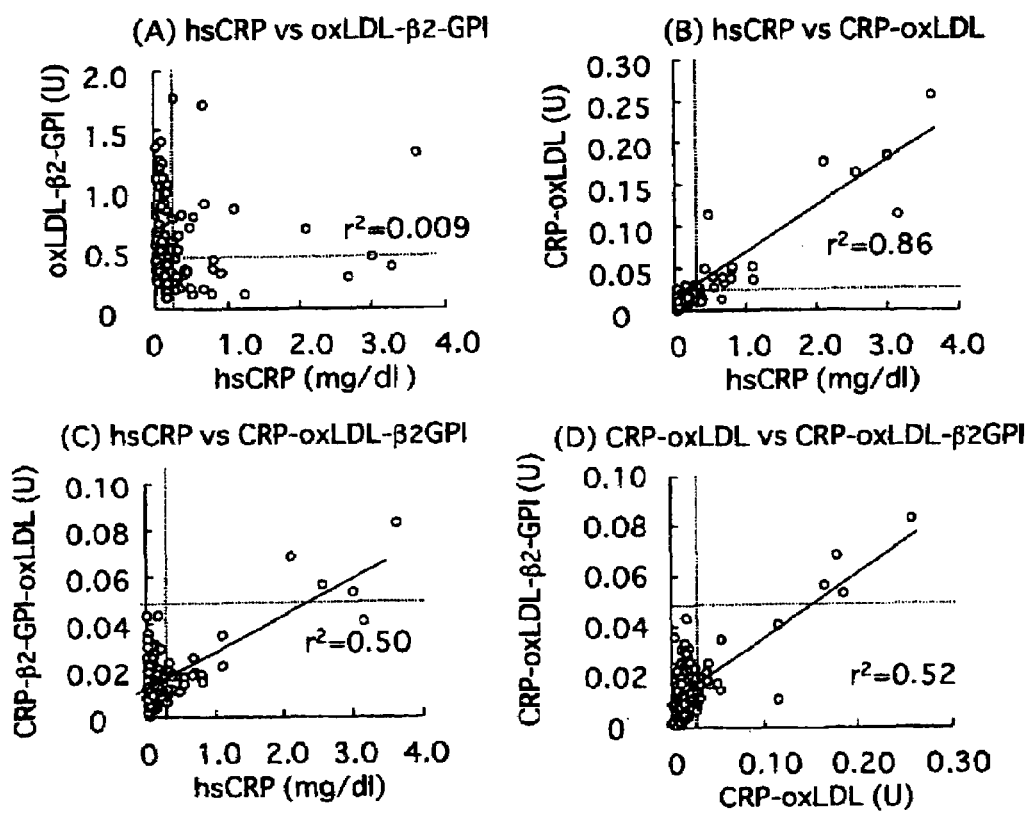
FIG. 4 shows correlations between the measuring methods with respect to the results of measurements of the sera of the patients in FIG. 3. Graph (A) shows the correlation between the measured value of CRP and the measured value of the oxLDL-β2-GPI complex, graph (B) shows the correlation between the measured value of CRP and the measured value of CRP-oxLDL complex, graph (C) shows the correlation between the measured value of CRP and the measured value of the CRP-oxLDL-β2-GPI complex, and graph (D) shows the correlation between the measured value of the CRP-oxLDL complex and the measured value of the CRP-oxLDL-β2-GPI complex.
Figure 5:
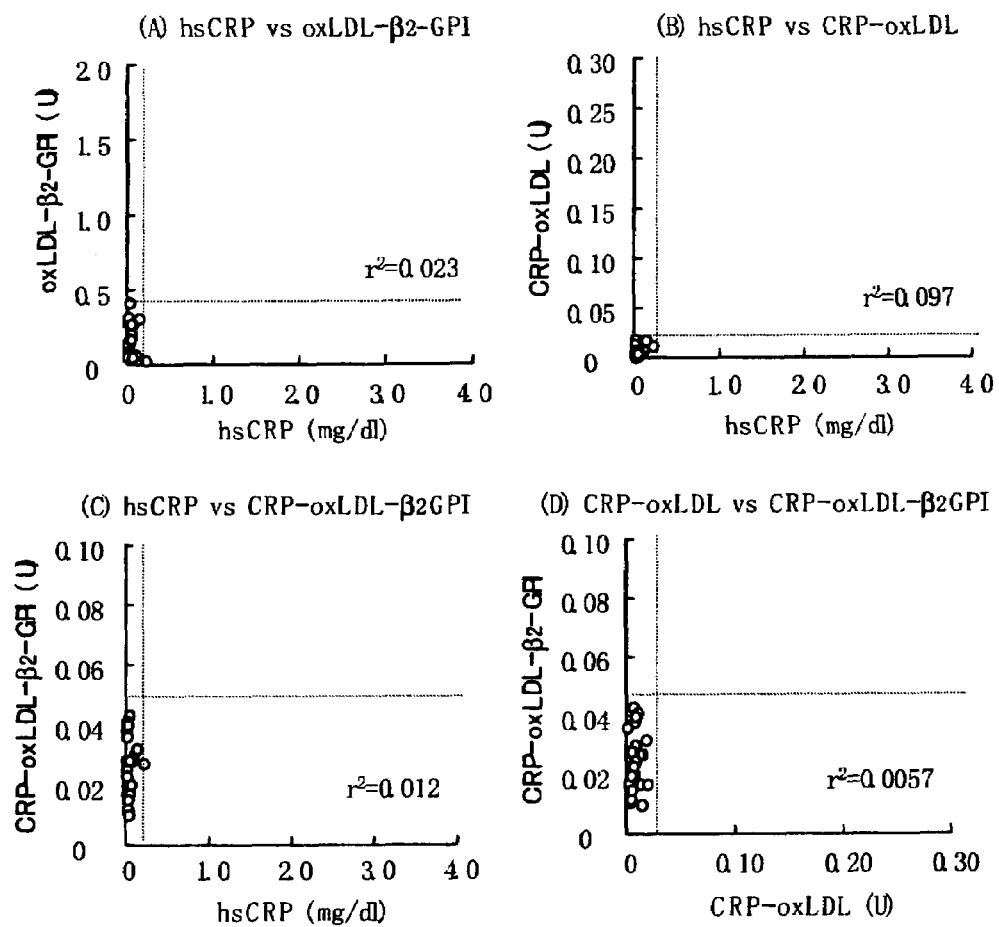
FIG. 5 shows correlations between the measuring methods with respect to the results of measurements of the sera of the normal persons in FIG. 3. Graph (A) shows the correlation between the measured value of CRP and the measured value of the oxLDL-β2-GPI complex, graph (B) shows the correlation between the measured value of CRP and the measured value of CRP-oxLDL complex, graph (C) shows the correlation between the measured value of CRP and the measured value of the CRP-oxLDL-β2-GPI complex, and graph (D) shows the correlation between the measured value of the CRP-oxLDL complex and the measured value of the CRP-oxLDL-β2-GPI complex.

FIGS. 3, 4 and 5 shows results of clinical analysis by measuring hsCRP (high sensitivity CRP), oxLDL-β2-GPI complex, CRP-oxLDL complex and CRP-oxLDL-β2-GPI complex in the sera of normal persons (28 cases) and diabetic patients (138 cases).

As shown in these three graphs, clinical cases showing higher values with respect to any of the hsCRP, oxLDL-β2-GPI complex, CRP-oxLDL complex and CRP-oxLDL-β2-GPI complex in sera were observed in the group of the diabetic patients as compared with the group of normal persons. hsCRP is CRP showing a minute quantity of changes that is measurable by a high sensitivity measuring system, and is distinguished from CRP synthesized in the liver in an acute inflammatory phase. hsCRP is considered to be produced by macrophages and smooth muscle cells of the blood vessel.

As shown in FIG. 4, significant correlation was found among the measured values of the hsCRP, CRP-oxLDL complex and CRP-oxLDL-β2-GPI complex. On the other hand, the oxLDL-β2-GPI complex showed correlation with neither hsCRP nor CRP-oxLDL complex.

These experimental results may lead to the following ideas.

In the diabetic patients, oxLDL formed by some oxidative stress binds, independently from $Ca^{2+}$, to β2-GPI that steadily circulates in the blood to form a complex. On the other hand, CRP that has been produced by a different mechanism from oxLDL forms a $Ca^{2+}$ dependent complex with oxLDL. Both reactions concerning formation of these two kinds of the complexes are advanced without any influences with each other. While either oxLDL caused by oxidative stress or hsCRP is known to be a risk factor for arteriosclerosis, it was made clear by the present invention that β2-GPI forms a complex with both of them.

Accordingly, the CRP-oxLDL complex or CRP-oxLDL-β2-GPI complex may be a new risk factor of arteriosclerosis encompassing known two risk factors—hsCRP and oxLDL.

Currently, a latex coagulation method using beads on which the anti-CRP antibody is immobilized has been mainly used for measuring hsCRP. However, since the sera of patients of arteriosclerosis and diabetes are often chylous due to hyperlipidemia, the chyle is known to affect the measuring system. Although a pretreatment may be applied to the sample using a removal reagent or centrifugation, it has been reported that this removal may decrease LDL. The measuring method of the present invention is highly possible to eliminate false negative ascribed to extinction of LDL since no pretreatment is necessary in the measuring method of the present invention.

From the results above, one of the examples of standard methods comprises the following steps.

(a) an anti-apoB monoclonal antibody (8 μg/ml, diluted with HBS) or anti-β2-GPI monoclonal antibody (8 μg/ml, diluted with HBS) is added to the ELISA plate in a proportion of 50 μl/well, and the antibody is immobilized to the well by allowing to stand at 4° C. overnight with hermetic sealing.

(b) Each well is washed three times by adding 200 μl/well of HBS containing 0.05% of Tween 20 (T-HBS).

(c) HBS containing 2% of BSA is added to each well in a proportion of 200 μl/well, and the plate is allowed to stand at room temperature for 1 hour.

(d) The serum diluted 100-fold with solution A is added to the ELISA plate in a proportion of 100 μl/well. In a separate run, the β2-GPI-oxLDL complex and CRP is pre-incubated at 37° C. in solution A, and is sequentially diluted with solution A to prepare solutions for preparing a standard curve. These solutions are added to each well of the ELISA plate in a proportion of 100 μl/well, and the plate is allowed to stand at 37° C. for 2 hours.

(e) Each well is washed with T-HBS three times.

(f) An HRP-labeled anti-CRP antibody with a concentration of 1 mg/ml is diluted 10,000-fold with solution A, and is added to each well in a proportion of 100 μl/well followed by allowing standing at room temperature for 1 hour.

(g) The well is washed three times with T-HBS.

(h) A solution, prepared by dissolving 4 mg of o-phenylenediamine in 10 ml of 0.1 M citrate buffer (pH 5.0) and mixed with 10 μl of 30% hydrogen peroxide, was added in each well in a proportion of 100 μl/well to develop a color by allowing the plate at room temperature for 15 minutes.

(i) The coloring reaction is stopped by adding 1M sulfuric acid, and absorbance at 490 nm is measured.

4. Preparation of Kit of the Present Invention (1) A kit of the present invention having the following constitution was prepared:

| | |
|---|---|
| 1. 96-well immunoplate | 1 plate |
| 2. anti-β2-GPI antibody (WB-CAL-1) | 1 vial |
| 3. HRP-labeled anti-human CRP antibody | |
| 4. o-phenylenediamine solution | 1 vial |
| 5. aqueous hydrogen peroxide | 1 vial |
| 6. reaction stopper solution (1N HCl) | 1 vial |
| 7. β2-GPI-oxLDL-CRP (standard) | |

(2) A kit of the present invention having the following constitution was prepared:

| | |
|---|---|
| 1. 96-well immunoplate | 1 plate |
| 2. anti-apoB antibody (N2E10) | 1 vial |
| 3. HRP-labeled anti-CRP antibody | |
| 4. o-phenylenediamine solution | 1 vial |
| 5. aqueous hydrogen peroxide | 1 vial |
| 6. reaction stopper solution (1N HCl) | 1 vial |
| 7. oxLDL-CRP (standard) | |

INDUSTRIAL APPLICABILITY

The detection method of the present invention is quite useful since various diseases including arteriosclerosis and diabetes can be detected by measuring the oxLDL-CRP complex. The kit of the present invention is also quite useful since the measuring method and detection method of the present invention can be more simply, promptly and easily executed.

The invention claimed is:

1. A method for measuring a complex of oxidized LDL, β2-GPI and CRP in a body fluid, which comprises:
    contacting an antibody A with the body fluid to bind said complex to said antibody A;
    contacting an antibody B with said complex which is bound to said antibody A, to further bind said complex to said antibody B; and
    detecting said complex which is bound to said antibody A and said antibody B,
    wherein said antibody A is an anti-β2-GPI antibody; and said antibody B is an anti-CRP antibody.

2. The method according to claim 1, wherein said antibody A is immobilized on a solid phase.

3. The method according to claim 1, wherein said antibody B is labeled, and said complex is detected by detecting the presence of the labeled antibody B bound to said complex which is bound to said antibody A and said antibody B.

* * * * *